United States Patent [19]

Inagaki et al.

[11] Patent Number: 4,708,951
[45] Date of Patent: Nov. 24, 1987

[54] ANTICOAGULATIVE HIGH-MOLECULAR COMPOSITIONS

[75] Inventors: Hiroshi Inagaki; Takeaki Miyamoto, both of Nagaokakyo; Hiraku Ito, Kyoto; Tohru Shibata, Himeji, all of Japan

[73] Assignee: Daicel Chemical Industries Ltd., Osaka, Japan

[21] Appl. No.: 715,658

[22] Filed: Mar. 25, 1985

[30] Foreign Application Priority Data

Mar. 28, 1984 [JP] Japan .................................. 59-62048

[51] Int. Cl.$^4$ ............................................ A61K 31/70
[52] U.S. Cl. ........................................ 514/57; 536/32; 536/57; 536/58
[58] Field of Search ...................... 514/57; 536/32, 58, 536/59

[56] References Cited

U.S. PATENT DOCUMENTS 4,299,817 11/1981 Hannan, III et al. ................. 424/70

Primary Examiner—Johnnie R. Brown
Assistant Examiner—Elli Peselev
Attorney, Agent, or Firm—Stiefel, Gross, Kurland & Pavane

[57] ABSTRACT

Anticoagulative high-molecular composition which comprises a cellulosic polyelectrolyte complex formed from a polycationic cellulose derivative such as a quaternary ammonium salt of hydroxyalkyl cellulose, and a polyanionic cellulose such as sodium cellulose glycolate, which is used in the field of medical instruments or devices.

15 Claims, 5 Drawing Figures

ANTICOAGULATIVE HIGH-MOLECULAR COMPOSITIONS

BACKGROUND OF THE INVENTION

1. Field of the Invention

The present invention relates to anticoagulative high-molecular compositions, more particularly, high-molecular compositions having an anticoagulative property which comprise as the main component a cellulosic polyelectrolyte complex formed from a polycationic cellulose derivative and a polyanionic cellulose derivative.

2. Description of the Prior Art

Hitherto, various plastic materials have been used in the field of medical instruments or devices such as various kinds of catheters, cannulae, tubes, blood-stocking containers, injectors, etc., as well as artificial internal organs, external circulation-aiding apparatuses and the like. The biggest problem encountered with the known materials was that the materials caused coagulation of blood as they came into contact with blood. Although it is known that such blood coagulation results from the contact of a blood protein called "contact factor" with the surface of an alien substance, the particular mechanism of the coagulation is still not clear. Therefore, it is not well known at the present time what types of materials are anticoagulative.

At present, the following three methods are used to obtain anticoagulative materials:

(1) Synthesizing high-molecular materials provided with those features which are considered favorable to anticoagulative properties, (2) Adding or bonding an anticoagulative, physiologically active substance to or with a synthetic material, and (3) Preparing a medical instrument with a living body per se.

Method (3) is, for example, a method of extracting and grafting an endothelial layer which is prepared by burying a high-molecular material in the body of an animal. However, the method is difficult to carry out on an industrial scale.

Method (2) is, more particularly a method of blending or bonding heparin, a water soluble polysaccharide functioning as an anticoagulative which is present in the body of animals, with a high-molecular material. However, it is difficult to maintain the original anticoagulative activity of heparin, probably because the functional groups of the heparin are partially consumed by the process of bonding the heparin with the surface of the high-molecular material. Moreover, such method is poor in productive and processing abilities. Also in the case of blending, heparin is not effective unless it appears on the surface of the material and, on the other hand, heparin present on the surface of the material is easily eluted, and so there arises a problem that coagulation is insufficient on bleeding or that the maintaining of coagulative activity for a long time is difficult.

Thus, it is most desirable to obtain anticoagulative materials by the synthetic method (1). However, there are no known materials, which meet the requirements of having those properties which are considered favorable to anticoagulative activity, such as suitable hydrophilic/hydrophobic balance, surface electric charge, etc., that they should be easily processed on molding, that they should have good affinity for blood, and that they are not dissolved or eluted, in or by blood.

It has now been found by the inventors of the present invention that polyelectrolytic cellulose complexes, which can be formed by mixing a polycationic cellulose derivative and a polyanionic cellulose derivative in a solvent common to the two, are insoluble in water and blood and have an excellent anticoagulative property. Cellulosic polyelectrolyte complexes are known to be effective for hair-dressing in the form of solution, though they are not yet isolated (U.S. Pat. No. 4,299,817 is referred to).

SUMMARY OF THE INVENTION

The present invention relates to an anticoagulative high-molecular composition comprising, as the main component, a cellulosic polyelectrolyte complex which is formed by mixing a polycationic cellulose derivative and a polyanionic cellulose derivative in a solvent common to the two.

DESCRIPTION OF THE PREFERRED EMBODIMENTS

Figure 1:
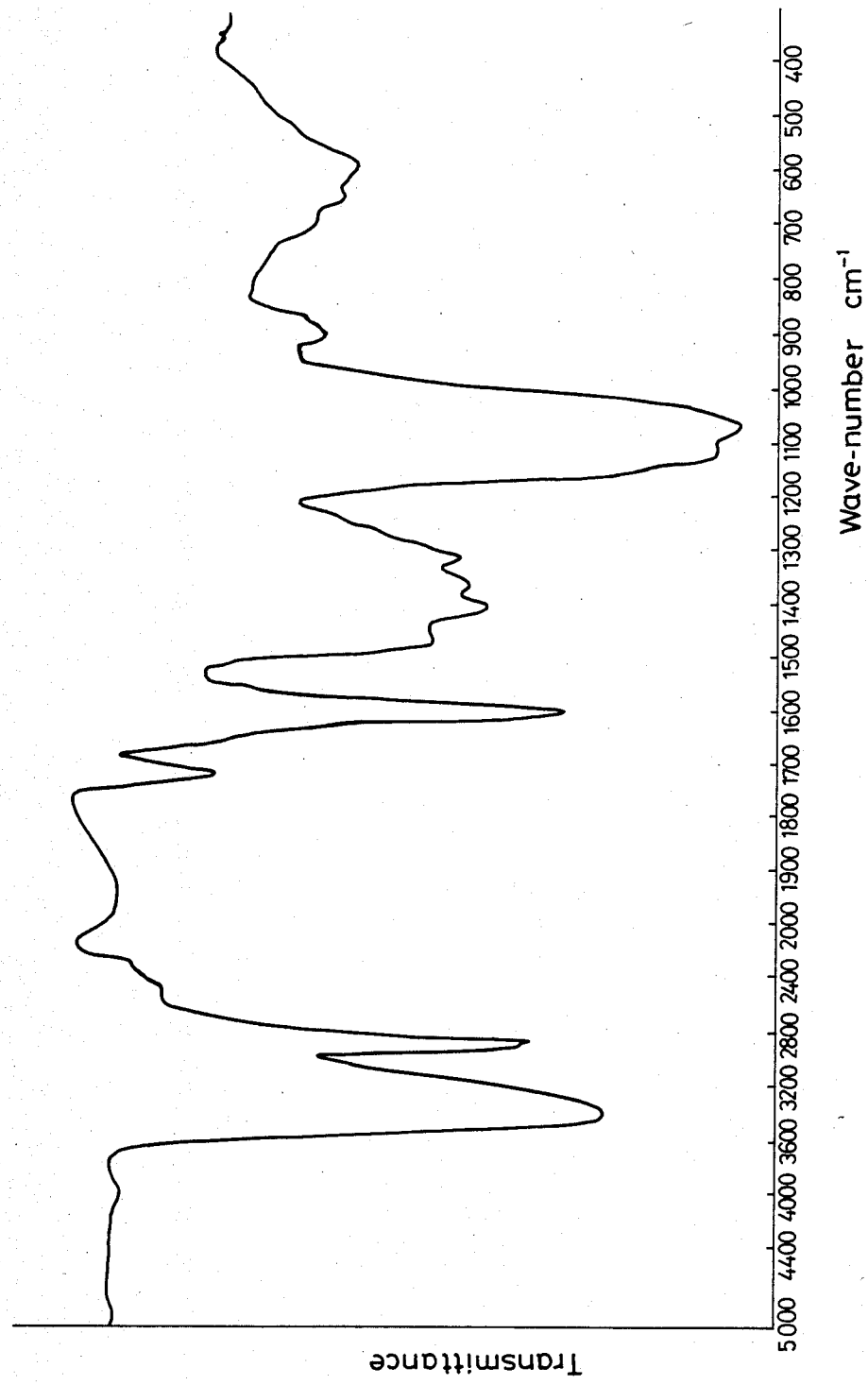
FIGS. 1–5 show an infrared spectrum of the polyelectrolytic cellulose complex obtained in Examples 1–5, respectively.

The polycationic cellulose derivative used in the present invention is a compound obtained by reacting cellulose or a cellulose derivative having free hydroxyl groups with an aminating agent such as diethylaminoethyl chloride, aminoethylsulfonic acid or the like, or with a cationizing agent of the quaternary ammonium salt type, such as glycidyl trimethylammonium halide, glycidyl triethylammonium halide, 3-chloro-2-hydroxypropyl trimethylammonium halide, aryl trimethylammonium halide or the like. More specifically, (β-hydroxy-γ-trimethylammonio propyl)cellulose chloride [QC], (β-hydroxy-γ-trimethylammoniopropyl)hydroxyethyl cellulose chloride [CTHEC], aminoethyl cellulose [AE], diethylaminoethyl cellulose [DEAE] and the like may be mentioned.

On the other hand, as the polyanionic cellulose derivative used in the present invention, there may be mentioned cellulose ethers or cellulose esters, such as sodium cellulose glycolate [CMC], sodium cellulose oxypropionate [CEC], sodium cellulose sulfate [CS], cellulose phosphate [CP] and the like.

Although these cellulose derivatives having polyelectrolytic ions are all soluble in water, they are also soluble in formic acid, trifluoroacetic acid, dimethylformamide (DMF), dimethyl sulfoxide (DMSO) and the like. Therefore, the polyelectrolytic complex can be formed by dissolving each component in a solvent common to the two components which is selected from the solvents mentioned above and mixing the two solutions. A particular process for the preparation of polyelectrolytic complexes is as follows:

(a) The polycationic cellulose derivative and the polyanionic cellulose derivative are separately dissolved in formic acid, and the two solutions are mixed together. Alternatively, the two derivatives are mixed by dissolving them simultaneously in formic acid. Although in some combinations of the two derivatives the resulting mixture becomes somewhat turbid as the complex is formed, it is considered that the state of dissolution is maintained. The complex molded in the form of a film is obtained by spreading the resulting solution and removing formic acid by evaporation (dry method), or by dipping the spread solution in a solvent which is compatible with formic acid and does not dissolve the complex (for example, water) to remove formic acid by extraction (wet method).

(b) When an aqueous solution of the polycationic cellulose derivative and an aqueous solution of the polyanionic cellulose derivative are mixed together, the complex is formed and precipitated. That is, the polyelectrolyte complex is insoluble in water. By centrifugal separation and drying, the complex is obtained in amorphous form. Since the complex is soluble in formic acid, the amorphous complex is dissolved in formic acid and from the formic acid solution the complex can be obtained molded in the form of film according to the manner described in (a).

It is not necessarily required to carry out the preparation of the complex according to the process (a) or (b) under equal electric charge. Either the polycationic cellulose derivative or the polyanionic cellulose derivative may be used in excess. From the results of experiments, the complex formed is insoluble in water and can be used as anticoagulative material even when either one of the two cellulose derivatives is used in an amount almost twice as much as the other.

When DMSO is added to the formic acid solution of the cellulosic polyelectrolyte complex in amount of one-tenth or less of the latter, the film obtained by spreading the resulting solution and removing the solvent has a higher equilibrium water content (hygroscopic property) than that prepared without adding DMSO.

The cellulosic polyelectrolyte complexes of the present invention, being soluble in solvents, can be molded into film, tube or the like according to the dry or wet method, or can be used for coating the surface of those widely used plastics such as polyolefin, polyvinyl chloride, polyester and the like to give them anticoagulative property. Such processing may be performed easily, because the cellulosic polyelectrolyte complexes of the present invention, being different from complexes formed from other synthetic high-molecules, are soluble in a single volatile solvent.

The polyanionic cellulose derivatives used in the present invention are those mainly used for food, medicine and the like and the polycationic cellulose derivatives used are those used for cosmetics. Both the polyanionic and polycationic cellulose derivatives are known to be physiologically harmless. Therefore, it is considered that the cellulosic polyelectrolyte complexes obtained from the two derivatives are also physiologically harmless.

Thus, the cellulosic polyelectrolyte complexes of the present invention have the following characteristics as high-molecular composition for medical use:

(1) Excellent anticoagulative properties,
(2) Applicable as coating material or molding material,
(3) Easily prepared from staple materials supplied on an industrial scale, and
(4) Considered to be low in toxicity and have affinity for a living body.

The anticoagulative properties of the high-molecular composition of the present invention is further demonstrated by the following Examples.

EXAMPLE 1

A polyelectrolyte complex of CTHEC and CMC

Seventy-one milliliters of a 1% aqueous solution of CTHEC (from UCC, MS=1.8, DS=0.4) and 29 ml of a 1% aqueous solution of CMC (from Daicel Chemical Industries, DS=0.85) were prepared separately; each solution was adjusted to a pH value of about 7, and then the two solutions were mixed while stirring gently. The resulting aqueous solution became turbid and an insoluble polyelectrolyte complex gel was formed. The gel was spread on a Teflon board and the water was evaporated by air-drying for several days, whereby a film having low transparency whose surface was not uniform was obtained. The weight of the film was 0.95 g after drying. The polyelectrolyte complex obtained was an equally electric charged complex. The film obtained was insoluble in water and isotonic sodium chloride solution.

The film obtained was dissolved again in 50 ml of formic acid and the solution was spread on a Teflon board, whereby a transparent, smooth and uniform film was obtained after air-drying for one day and night.

EXAMPLE 2

A polyelectrolyte complex of CTHEC and CMC

In 50 ml of formic acid 7.1 g of the same CTHEC as used in Example 1 and 2.9 g of the same CMC as used in Example 1 were dissolved and mixed together. By spreading the resulting solution on a Teflon board, a transparent, smooth and uniform film was obtained. An infrared absorption spectrum of the complex is shown in FIG. 1.

Anticoagulative property of the polyelectrolyte complex comprising CTHEC/CMC—Evaluation method 1, Lee-White method In a glass test tube for aggregation, having an inside diameter of 10 mm$\phi$ and meeting JIS, were taken several milliliters of the formic acid solution of Example 1, and the solution was adhered to the inside of the test tube in an amount sufficient to just coat it. The excess solution was discarded, and then the test tube was dried. Thus a test tube having a coating layer of the polyelectrolyte complex on its inside was prepared. One milliliter of fresh blood of a grown-up dog or an adult was poured into said test tube, and the time required until the blood lost its fluidity (coagulation time Tc) was measured by making observations of the state of blood at intervals of one minute. The coagulation time $T_G$ of blood in an uncoated glass test tube was also measured and the ratio of Tc/$T_G$ was calculated. The results obtained are shown in Table 1. The coagulation time was significantly extended by applying the coating with the polyelectrolyte complex to the inside of the test tube.

TABLE 1

| Test No. | Blood | Tc (minutes) | $T_G$ (minutes) | Tc/$T_G$ |
|---|---|---|---|---|
| 1 | dog | 44 | 9 | 4.9 |
| 2 | dog | 40 | 8 | 5.0 |
| 3 | dog | 47 | 6 | 7.8 |
| 4 | dog | 40 | 7 | 5.7 |
| 5 | human being | >70 | 10 | >7.0 |

Anticoagulative property of the polyelectrolyte complex comprising CTHEC/CMC—Evaluation method 2, method of inserting a coated suture in a peripheral vein A polyester suture for operation (International Standard No. 1–05) was cut into a length of 10 cm, coated with the formic acid solution of the polyelectrolytic complex of Example 1, and dried. The coated gut thus obtained was inserted into the femoral vein or the jugular vein of a grown-up dog and, after the lapse of the prescribed period (2 hours, and one day and night), the blood was removed by heparinization. Then, the vein was incised, washed with isotonic sodium chloride solution and observed with the eye to evaluate the state of its surface. The results are shown in Table 2. The gut coated with the polyelectrolyte complex of the present invention showed a significant anticoagulative property, also according to this evaluation method.

TABLE 2

| Sample | Degree of thrombosis | |
|---|---|---|
| | 2 hrs. | 1 day and night |
| coated gut | — | — |
| polyester gut | ++ | +++ |

—: No thrombus was formed,
+: Partial thrombosis,
++: Thrombosis over the whole surface,
+++: Massive thrombosis over the whole surface, causing obstruction of blood vessels.

EXAMPLE 3

A polyelectrolyte complex of CTHEC and CMC

Figure 2:
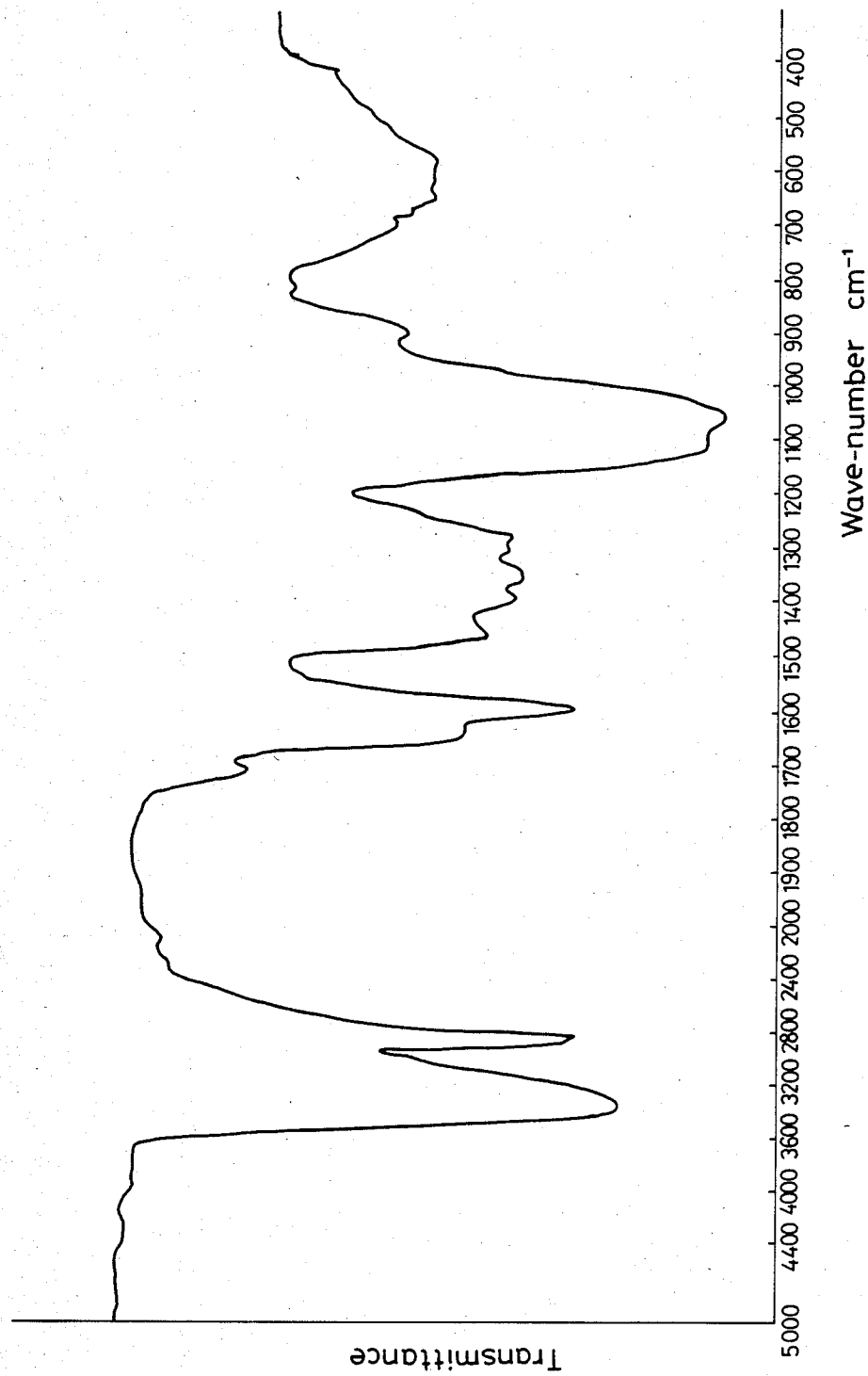

Using the same CTHEC and CMC as used in Example 1 but changing the amounts used, a polyelectrolyte complex containing an excess of cations was prepared. More particularly, 7.9 g of CTHEC and 2.1 g of CMC were dissolved in 50 ml of formic acid and mixed while stirring. By spreading the resulting solution on a Teflon board, a transparent, smooth film was obtained. This was a cation-excessive complex having positive charge: negative charge=1.5:1. An infrared absorption spectrum of the complex is shown in FIG. 2. The film obtained was insoluble in water and isotonic sodium chloride solution.

Figure 3:
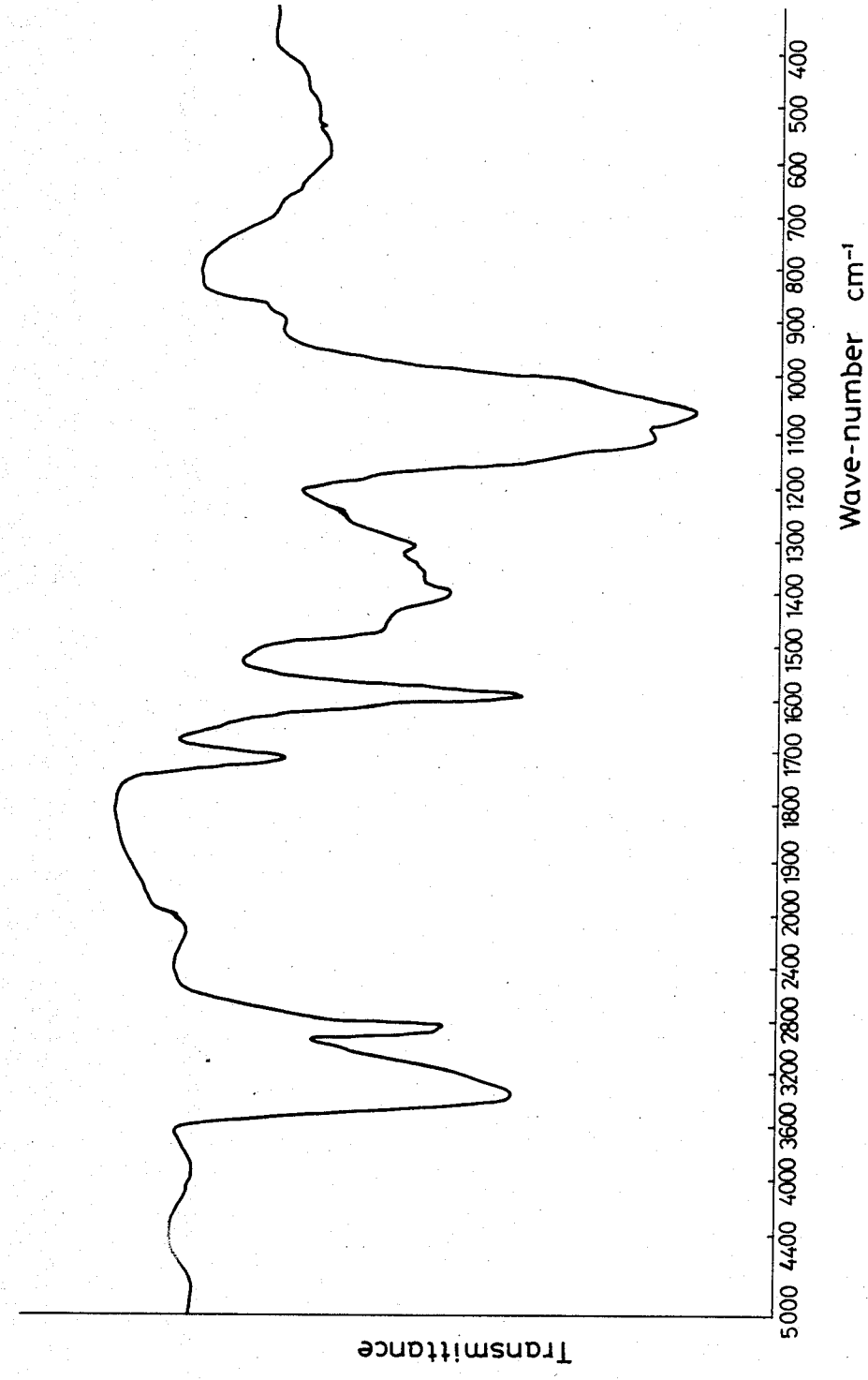

Next, an anion-excessive complex was prepared likewise. More particularly, 6.2 g of CTHEC and 3.8 g of CMC were dissolved and mixed in 50 ml of formic acid. By spreading the resulting solution on a Teflon board, a transparent, smooth film was obtained. This was an anion-excessive complex having positive charge: negative charge=1:1.5. The film obtained was insoluble in water and isotonic sodium chloride solution. An infrared absorption spectrum of the complex is shown in FIG. 3.

The two examples of unequally charged complexes thus obtained were subjected to an anticoagulative property test using blood of a grown-up dog according to the evaluation method 1. An equally charged complex was tested at the same time and the results compared. The results obtained are shown in Table 3. The anticoagulative property of the equally charged complex and the unequally charged complexes were almost identical.

TABLE 3

| | Sample | | | | | |
|---|---|---|---|---|---|---|
| | No. 1 | | No. 2 | | No. 3 | |
| | Tc (minutes) | Tc/T$_G$ | Tc (minutes) | Tc/T$_G$ | Tc (minutes) | Tc/T$_G$ |
| Polyelectrolyte complex coating | | | | | | |
| cation excessive | 31 | 3.5 | 29 | 4.1 | 39 | 4.9 |
| equally charged | 34 | 3.8 | 29 | 4.1 | 31 | 3.9 |
| anion excessive | 32 | 3.6 | 33 | 4.7 | 31 | 3.9 |
| Glass | (9) | 1.0 | (7) | 1.0 | (8) | 1.0 |

EXAMPLE 4

A polyelectrolyte complex of QC and CMC

Figure 4:
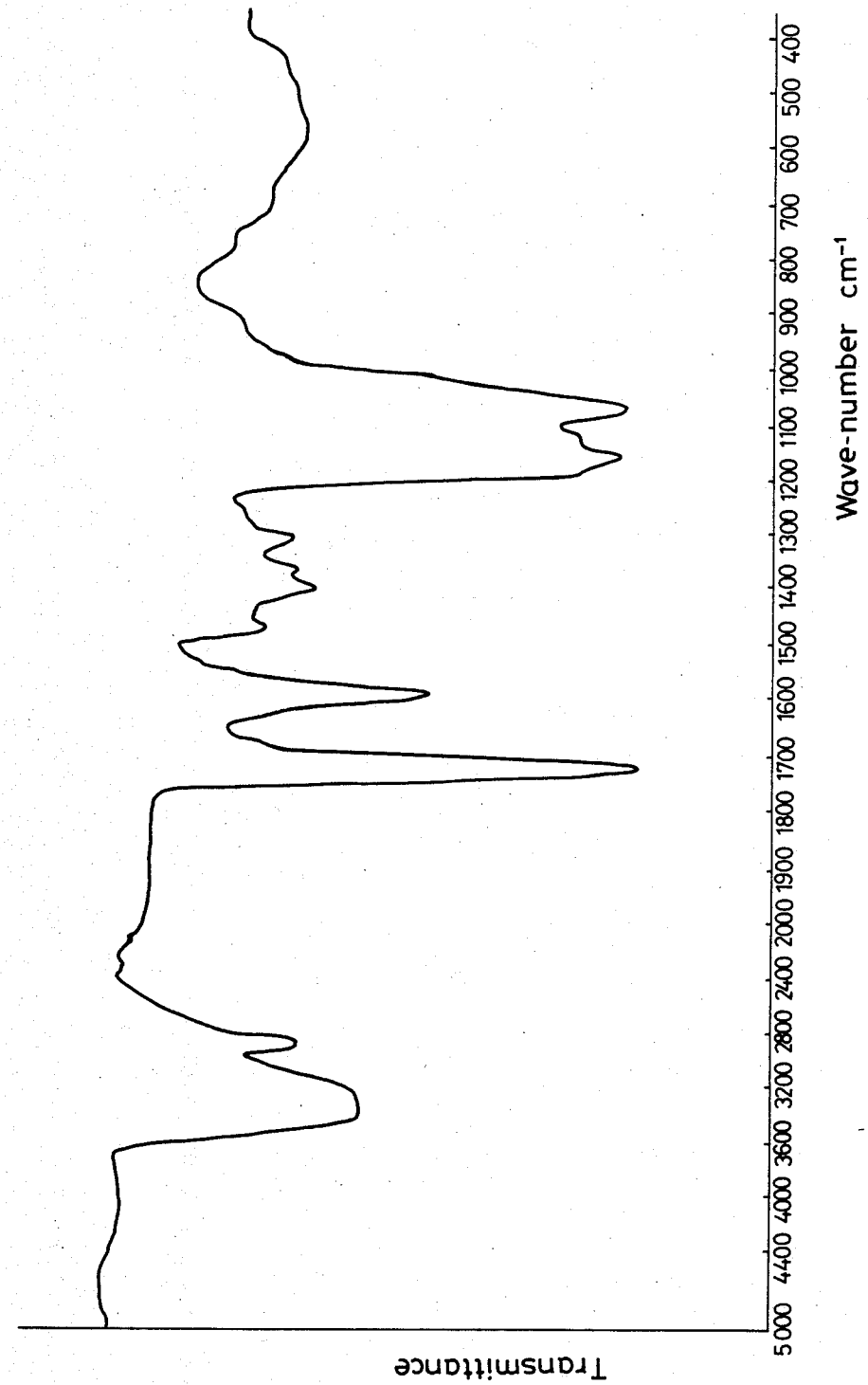

In 50 ml of formic acid 5.7 g of QC (from Daicel Chemical Industries, DS=0.4) and 4.3 g of CMC (from Daicel Chemical Industries, DS=0.85) were dissolved, and a film was prepared by spreading the solution on a Teflon board. The film was transparent and smooth, and was insoluble in water and isotonic sodium chloride solution. The complex is considered a substantially equally charged polyelectrolytic complex. An infrared absorption spectrum of the complex is shown in FIG. 4. The complex, which was evaluated according to the same method as evaluation method 1, showed excellent anticoagulative property. The results obtained are shown in Table 4.

EXAMPLE 5

A polyelectrolyte complex of CTHEC and CS

Figure 5:
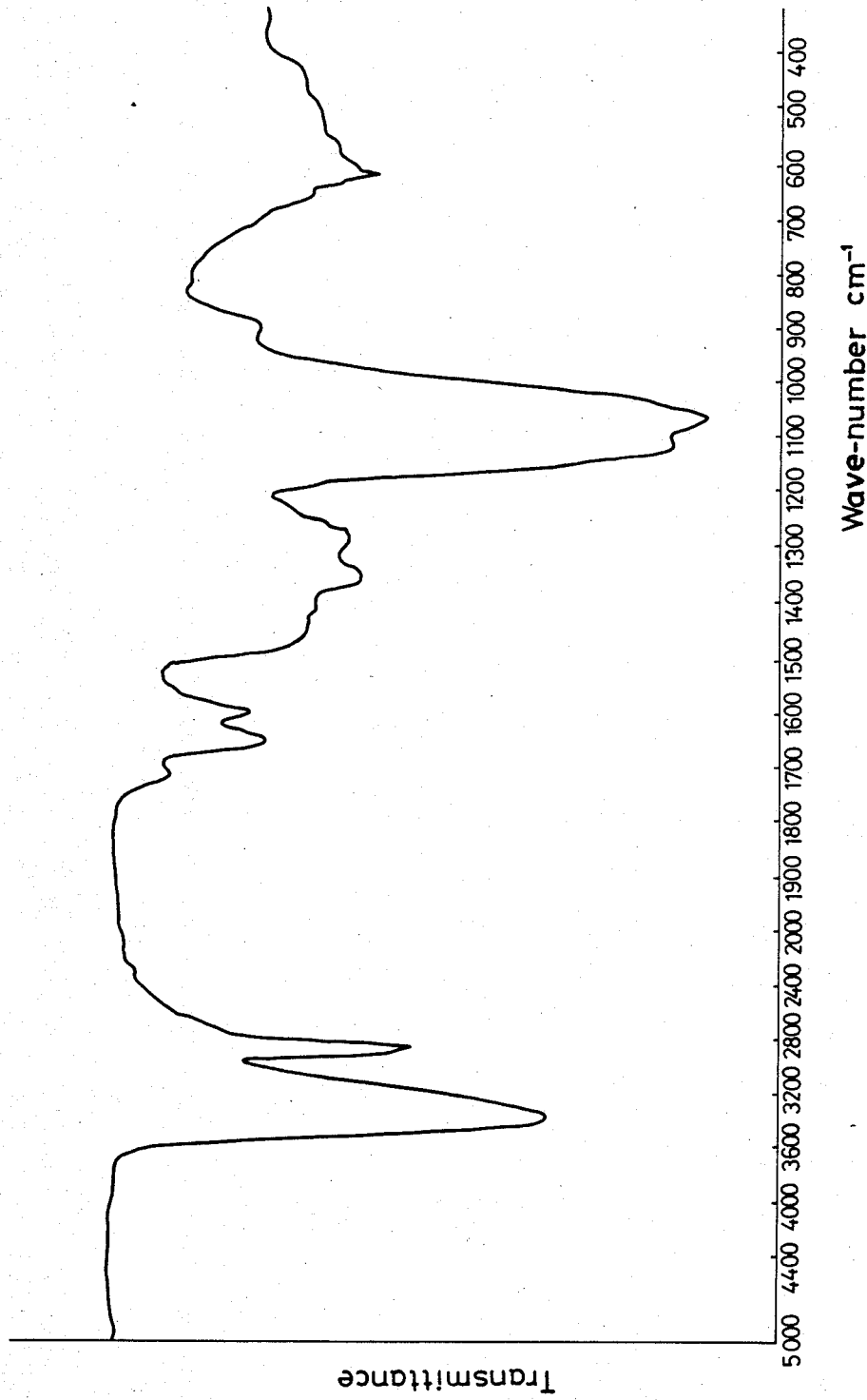

In 50 ml of formic acid 6.3 g of the same CTHEC (from UCC, MS=1.8, DS=0.4) as used in Example 1 and 3.7 g of CS (from Daicel Chemical Industries, DS=0.54) were dissolved, and a film was prepared by spreading the solution on a Teflon board. The film was transparent and smooth, and was insoluble in water and isotonic sodium chloride solution. An infrared absorption spectrum of the complex is shown in FIG. 5. The complex is considered a substantially equally charged polyelectrolyte complex.

The complex, which was evaluated by the same method as evaluation method 1, showed excellent anticoagulative property. The results obtained are shown in Table 4.

TABLE 4

| | Sample | | | | | |
|---|---|---|---|---|---|---|
| | No. 1 | | No. 2 | | No. 3 | |
| | Tc (minutes) | Tc/T$_G$ | Tc (minutes) | Tc/T$_G$ | Tc (minutes) | Tc/T$_G$ |
| QC/CMC | 40 | 5.0 | 34 | 4.9 | 37 | 4.1 |
| CTHEC/CS | 37 | 4.6 | 37 | 5.3 | | |

TABLE 4-continued

| | Sample | | | | | |
|---|---|---|---|---|---|---|
| | No. 1 | | No. 2 | | No. 3 | |
| | Tc (minutes) | Tc/T$_G$ | Tc (minutes) | Tc/T$_G$ | Tc (minutes) | Tc/T$_G$ |
| Glass | (8) | 1.0 | (7) | 1.0 | (9) | 1.0 |

What we claimed is:

1. An anticoagulative high-molecular composition which comprises a cellulosic polyelectrolyte complex formed from (1) a polycationic cellulose derivative selected from the group consisting of a quaternary ammonium salt of a hydroxyalkyl cellulose, aminoethylcellulose and diethylaminoethylcellulose, and (2) a cellulose ether or cellulose ester polyanionic cellulose derivative.

2. The anticoagulative high-molecular composition of claim 1, wherein the polyanionic cellulose derivative is a cellulose ether or cellulose ester selected from sodium cellulose glycolate, sodium cellulose oxypropionate, sodium cellulose sulfate and cellulose phosphate.

3. The anticoagulative high-molecular composition of claim 1, wherein the polycationic cellulose derivative and the polyanionic cellulose derivative are present in the polyelectrolyte complex in equal electric charge amounts.

4. The anticoagulative high-molecular composition of claim 1, wherein said composition is molded in the form of a film or tube.

5. The anticoagulative high-molecular composition of claim 1, wherein said composition is a film coated on an inner surface of a tube.

6. The anticoagulative high-molecular composition of claim 1, wherein the polycationic cellulose derivative is a quaternary ammonium salt of a hydroxyalkyl cellulose.

7. The anticoagulative high-molecular composition of claim 6, wherein the quaternary ammonium salt of a hydroxyalkyl cellulose is ($\beta$-hydroxy-$\gamma$-trimethylammonio propyl)cellulose chloride or ($\beta$-hydroxy-$\gamma$-trimethylammonio propyl)hydroxyethyl cellulose chloride.

8. The anticoagulative high-molecular composition of claim 1, wherein the polycationic cellulose derivative or the polyanionic cellulose derivative is present in the polyelectrolyte complex in excess, the polyelectrolyte complex formed therefrom having an anionic or cationic excess in an amount of almost 2:1.

9. A method of treating blood for preventing coagulation of said blood comprising contacting the blood with a surface comprising an effective amount of a cellulosic polyelectrolyte complex for imparting anticoagulative properties to said surface, the complex being formed from (1) a polycationic cellulose derivative comprising a reaction product of cellulose or a cellulose derivative having free hydroxyl groups with an aminating agent, or with a quaternary ammonium salt cationizing agent; and (2) a cellulose ether or cellulose ester polyanionic cellulose derivative.

10. The method of claim 9, wherein the polycationic cellulose derivative is selected from a quaternary ammonium salt of a hydroxyalkyl cellulose, aminoethylcellulose and diethylaminoethylcellulose.

11. The method of claim 10, wherein the polycationic cellulose derivative is a quaternary ammonium salt of a hydroxyalkyl cellulose.

12. The method of claim 11, wherein the quaternary ammonium salt of a hydroxyalkyl cellulose is ($\beta$-hydroxy-$\gamma$-trimethylammonio propyl)cellulose chloride or ($\beta$-hydroxy-$\gamma$-trimethylammonio propyl)hydroxyethyl cellulose chloride.

13. The method of claim 9, wherein the polyanionic cellulose derivative is a cellulose ether or cellulose ester selected from sodium cellulose glycolate, sodium cellulose oxypropionate, sodium cellulose sulfate and cellulose phosphate.

14. The method of claim 9, wherein the polycationic cellulose derivative and the polyanionic cellulose derivative are present in the polyelectrolyte complex in equal charge amounts.

15. The method of claim 9, wherein the polycationic cellulose derivative or the polyanionic cellulose derivative is present in the polyelectrolyte complex in excess, the polyelectrolyte complex formed therefrom having an anionic or cationic excess an amount of almost 2:1.

* * * * *